(12) United States Patent
Abramov

(10) Patent No.: US 9,144,674 B2
(45) Date of Patent: Sep. 29, 2015

(54) PIEZO-ELECTRIC DEFIBRILLATION SYSTEM

(71) Applicant: Igor Abramov, Vista, CA (US)

(72) Inventor: Igor Abramov, Vista, CA (US)

( * ) Notice: Subject to any disclaimer, the term of this patent is extended or adjusted under 35 U.S.C. 154(b) by 0 days.

(21) Appl. No.: 14/219,247

(22) Filed: Mar. 19, 2014

(65) Prior Publication Data

US 2014/0288574 A1 Sep. 25, 2014

Related U.S. Application Data

(60) Provisional application No. 61/804,702, filed on Mar. 24, 2013.

(51) Int. Cl.
*A61N 1/39* (2006.01)
*A61N 1/05* (2006.01)

(52) U.S. Cl.
CPC ............... *A61N 1/0504* (2013.01); *A61N 1/39* (2013.01)

(58) Field of Classification Search
CPC ....... A61N 1/046; A61N 1/0563; A61N 1/39; A61N 1/0504

USPC ....................................... 607/5, 115, 142, 145
See application file for complete search history.

(56) References Cited

U.S. PATENT DOCUMENTS

| | | | |
|---|---|---|---|
| 2004/0186545 A1* | 9/2004 | Rosero et al. | 607/119 |
| 2005/0288716 A1* | 12/2005 | Zsigmond | 607/5 |
| 2010/0042137 A1* | 2/2010 | Oronsky et al. | 606/204 |
| 2013/0226260 A1* | 8/2013 | Brenner et al. | 607/35 |
| 2014/0288573 A1* | 9/2014 | Abramov | 606/129 |

\* cited by examiner

*Primary Examiner* — Theodore Stigell
*Assistant Examiner* — Michael Carey

(57) ABSTRACT

Disclosed are several embodiments of a battery-less piezo-electric defibrillation system (2) comprising external piezo-electric defibrillator (4) and at least one electrode (5) connected thereto. The system includes a piezo-electric generator (6) connected to direct cardiac access—(5), or indirect subcutaneous electrode assemblies (30). The piezo-electric generator (6) is energized by a spring-driven striker element (8) and produces electrical pulse for defibrillation. The direct cardiac access electrodes (5) engage the heart muscle directly via the intercostal space. Alternatively, indirect subcutaneous electrodes (34a) are positioned under patient's skin.

17 Claims, 9 Drawing Sheets

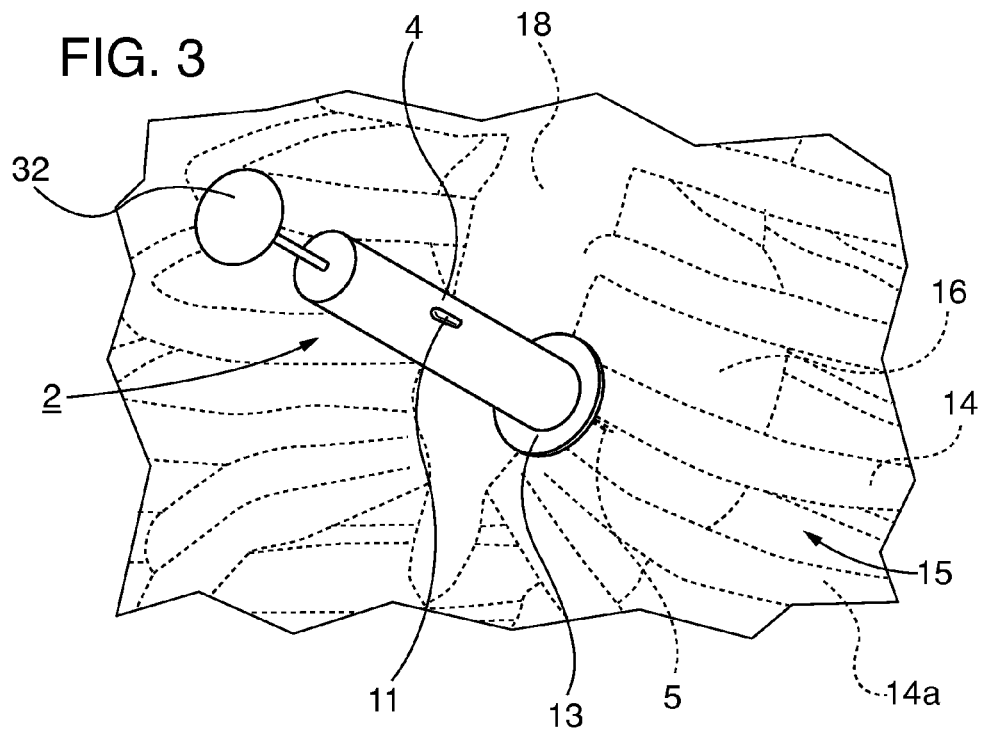
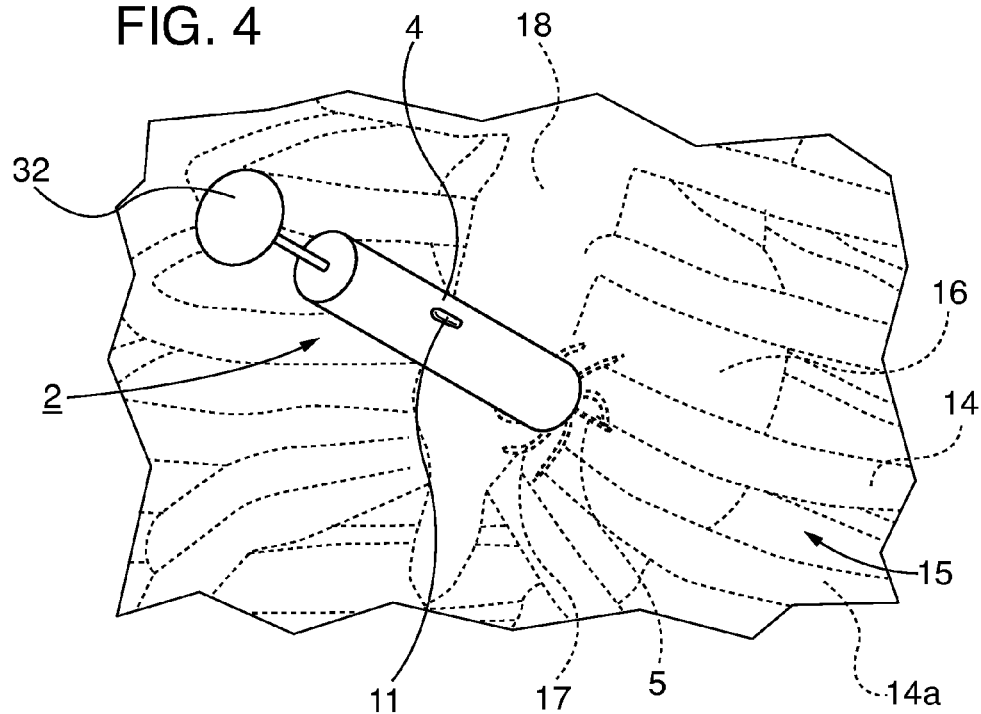

FIG. 18
PRIOR ART
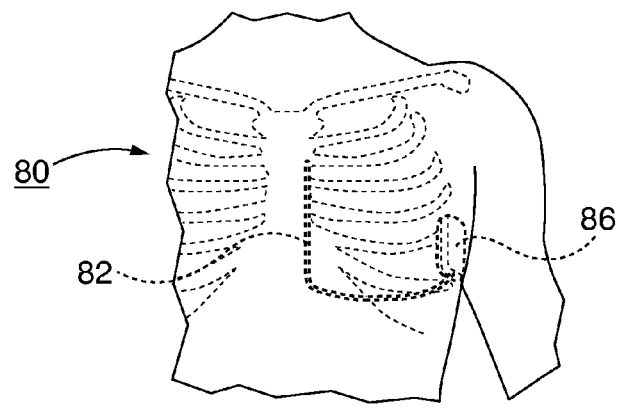
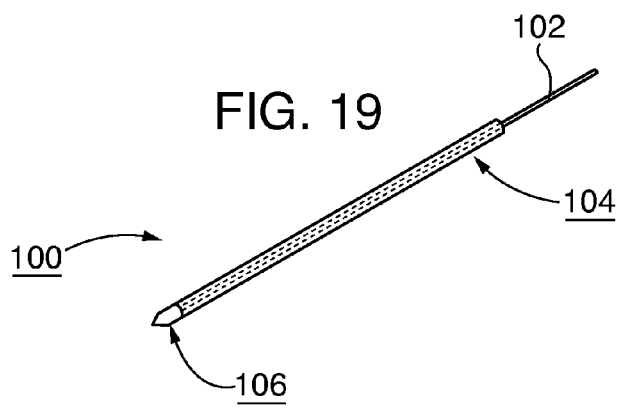
FIG. 19
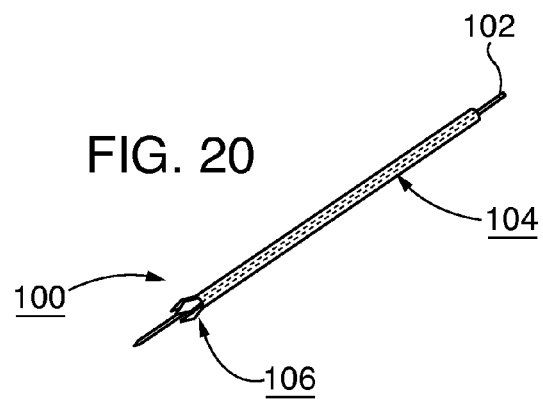
FIG. 20

PIEZO-ELECTRIC DEFIBRILLATION SYSTEM

FIELD OF INVENTION

This invention relates in general to cardiac defibrillators, and in particular to external portable defibrillators and systems not requiring a battery source.

BACKGROUND OF INVENTION

Modern emergency medical practice strives to provide the most advanced and timely diagnosis and treatment as possible, since time factor is often crucial to the successful clinical outcomes.

One of the sudden critical health crises is cardiac ventricular fibrillation (VF) which is invariably fatal unless treated promptly. The common way to treat VF is to administer an electric pulse to the heart which shocks the heart muscle and induces it to revert to its normal contraction pattern. This procedure is called defibrillation and is effected by an apparatus called 'defibrillator'.

There are two types of defibrillators: the external and internal, the latter implanted into a patient's body.

External defibrillators are relatively large and contain a large battery pack and a high voltage generator. The weight of an external defibrillator is in the order of 2-3 lbs (1-1.5 kg). The generated high voltage pulse is administered to a patient via two large conductive paddles positioned on his chest and side, respectively. The defibrillator batteries have to be periodically tested and if of the rechargeable type, recharged, which adds to the maintenance labor and expenses for the system's owner.

The implantable defibrillator, being very small and light is permanently surgically implanted into a patient's body, and its electrical lead is inserted into the heart. The outer case of the device is made of metal and acts as a second electrode to complete the path of electrical current through the heart. The implantable defibrillators are used in patients with chronic cardiac disease and their implantation requires a major surgical procedure in a hospital setting.

In an emergency situation providing an external defibrillator in a timely manner can be problematic, since due to its size and weight it presents a carry challenge to first-response medical personnel who are frequently over-burdened with other equipment and may not have an external defibrillator in their medical kit. Also, some first-responders, such as for example motorcycle patrol policemen may not carry a defibrillator due to the limited carry space on their motorcycles. Waiting for the response team with a defibrillator to arrive may spell death for the VF sufferer. On the other hand, to implant a small defibrillator under field conditions and within an extremely short 'window of opportunity' is not feasible.

Still, having a defibrillation capability 'on-hand' in an emergency is very desirable in view of its potential in saving lives.

In addition, it would be desirable to have a defibrillator system of the 'store-and-forget' type: the one not requiring any service, like periodic testing or re-charging of the batteries.

OBJECTIVES OF THE INVENTION

Thus, it is the objective of instant invention to provide a small and light defibrillator system which can be easily carried by a first-responder personnel along with other first-aid equipment.

Another objective is to provide a defibrillator system which would be easy to maintain and would offer a service-free virtually unlimited storage life.

Yet another objective is to provide a defibrillator which would be easy to use even by an untrained personnel.

SUMMARY OF THE INVENTION

In accordance with the present invention, a miniature battery-less piezo-electric defibrillation system is disclosed. The system consists of a small and light piezo-electric external defibrillator equipped with direct cardiac access-, or indirect subcutaneous electrodes, or both. These types of electrodes provide a low impedance electrical path to the patient's heart which lowers the energy required for defibrillation and enable compact defibrillator.

The direct cardiac access electrodes engage the heart muscle directly, preferably via the left $5^{th}$ intercostal space.

The subcutaneous-type electrodes are positioned below the skin near the patient's sternum and laterally below the left armpit. Their design also facilitates simplified operation by an untrained personnel.

PRIOR ART

The prior art is comprised by two distinct groups of defibrillators: the external and the implantable ones. The external ones, as was mentioned, are large and heavy for the wide availability in emergencies. The implantable defibrillators, while very small, are unsuitable in the first-response situations.

OBJECTS AND ADVANTAGES

In contrast to the prior art mentioned hereinabove, the present invention provides a miniature external defibrillator, which, together with the specific electrode system delivers the desired defibrillation action. In addition, the defibrillator does not require batteries to operate: the defibrillation energy is generated via mechanical stress on the piezo-electric generator element.

My research showed that a great difference exists between the required defibrillation energy while using an external defibrillator and using an implanted defibrillator. An external defibrillator is required to deliver up to 400 Joules of electrical energy per pulse. The need for high energy output for external defibrillation results in large size and weight of the corresponding defibrillators. In contrast, only 10-50 Joules per pulse are delivered by an implanted defibrillator with a direct intra-cardiac electrode, with satisfactory defibrillation results.

I determined that the difference in the required pulse energies is due to the high impedance of the human skin and tissues immediately underneath it, which needs to be overcome by the existing external defibrillators in order to deliver sufficient defibrillation energy to the heart.

If, however, the heart can be stimulated from within the body, such as done presently with implanted defibrillators, directly to/inside the heart, or from under the skin and thus avoiding its high impedance, the required pulse energy is greatly reduced.

Thus, it is possible to use a small external defibrillator if its energy is delivered directly to the heart or indirectly subcutaneously, avoiding high losses in the skin and the immediate underlying tissue.

Indeed, an implantable defibrillator, Model S-ICD® introduced recently by Boston Scientific, Inc. of Natick, Mass., USA utilizes an indirect subcutaneous electrode positioned along the sternum, with the defibrillator itself implanted laterally, below left armpit. The metal case of this defibrillator serves as a second subcutaneous electrode to complete the current path through the patient's heart. The energy generated by this device is relatively low 80 Joules per pulse but it is sufficient for successful defibrillation. This further supports the low-impedance model of subcutaneous electrode operation.

Additionally and crucially, the reduced defibrillation energy required, in the order of 50-80 Joules, allows the use of piezo-electric generators instead of batteries.

Furthermore, in case of external defibrillators, the external electrode pads by necessity are made quite large in order to decrease impedance and current density and avoid burns to the patient's skin. In case of subcutaneous electrodes, this requirement is reduced due to lower impedance.

Nevertheless, in several embodiments of the instant system, precautions were taken to decrease current density at electrodes to minimize a chance of an electrical burn injury to the patient.

BRIEF DESCRIPTION OF THE DRAWINGS

FIG. 3 is a perspective view of the defibrillation system positioned on the patient's thorax and engaging his heart.

FIG. 4 is a perspective view of the defibrillation system's alternate embodiment positioned on the patient's thorax and engaging his heart.

FIG. 18 is prior art of implantable defibrillator with indirect subcutaneous electrode.

FIG. 19 is a perspective view of a linear subcutaneous electrode assembly inside the introducer prior to insertion.

FIG. 20 is a perspective view of a linear subcutaneous electrode assembly inside the introducer, with introducer being extracted.

DESCRIPTION OF THE PREFERRED EMBODIMENT

Figure 1:
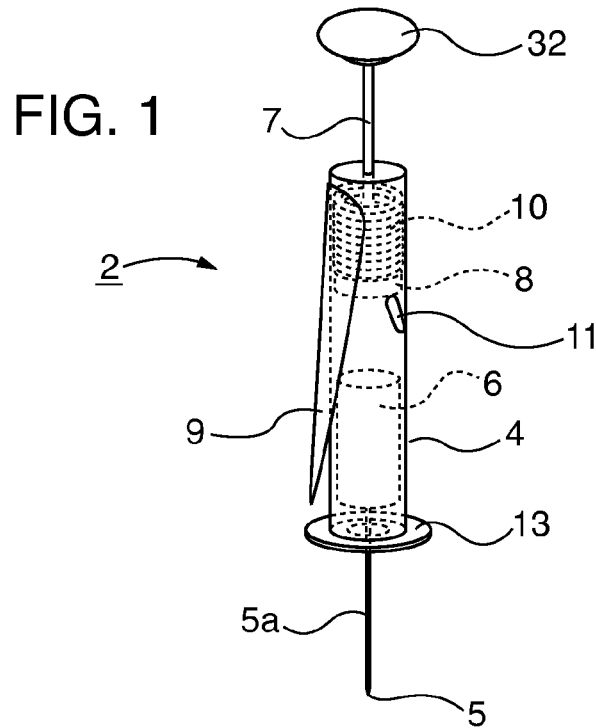
FIG. 1 is a perspective view of the defibrillator of the instant invention, in the armed configuration.
Figure 2:
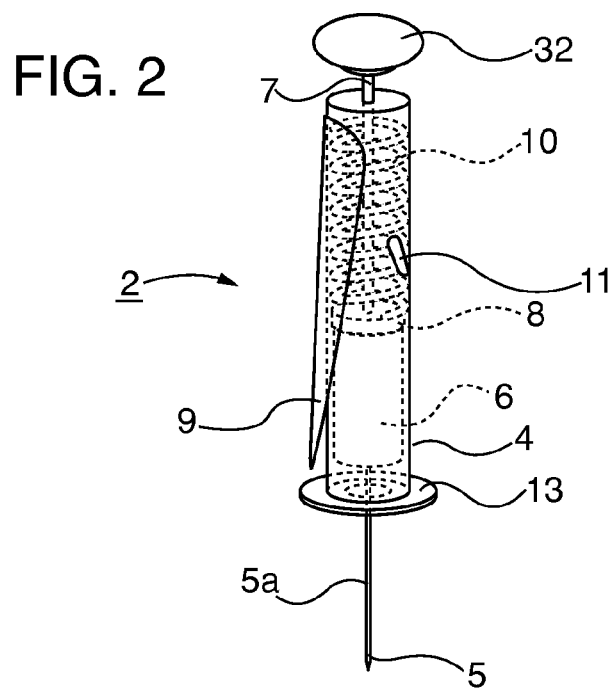
FIG. 2 is a perspective view of the defibrillator of the instant invention, in the fired configuration.

In the foregoing description like components are referenced by the like numerals. The preferred embodiment 2 of the defibrillator system is shown on FIGS. 1 and 2. Defibrillator 2 comprises cylindrical case 4 which houses piezo-electric generator 6, striker 8, power spring 10, and direct cardiac access electrode 5. Electrode 5 is covered with electrically insulating layer 5a, with the exception of its very tip which is made very sharp for easy penetration into patient's body.

Striker 8 is connected to handle 32 by shaft 7. On the outside of case 4 there is a hinged lever 9 which at its proximal end interacts with shaft 7. Lever 9 is sprung by spring 7b to enable its ratcheting action against shaft 7. Trigger 11 is pivotally attached to case 4 and holds striker 8 in armed position prior to its release.

Figure 5:
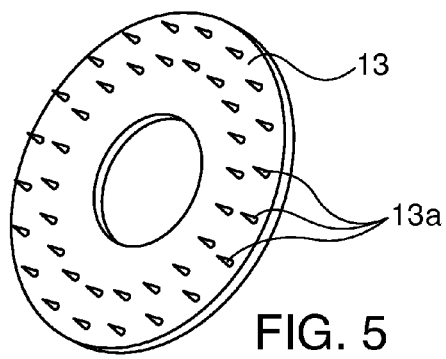
FIG. 5 is a perspective view of a 'return' electrode assembly with spike-shaped electrode elements.

Case 4 at its bottom is terminated by a generally annular 'return' electrode 13, which contains a plurality of sharp penetration spikes 13a on its bottom surface, as shown on FIG. 5.

One output of the piezo-electric generator 6 is connected to the electrode 13 and the other to the direct cardiac access electrode 5. An optional impedance-matching and output pulse shaping network preferably comprising a transformer 6a and passive resistor-inductor-capacitor ("R-L-C")-type network 6b is electrically interposed between generator 6 and electrodes 5 and 13. The primary and secondary windings of the transformer are labeled 'P' and 'S' respectively and contain equal or different number of wire turns, depending on the determined impedance match requirements.

Piezo-electric generator 6 can be realized with a number of piezo-electric materials, such as $BaTiO_3$, $LiNbO_3$, PMN-PT, PZT, PZN-9PT and the like, preferably as a stack of individual metallized elements. Such piezoelectric stacks used primarily for precision actuators and high voltage pulse generation are well-known in the art. The maximum conversion efficiency of power conversion from mechanical to electrical energy in piezo-electric materials occurs with maximum force and lowest frequency. Our preferred embodiment design calls for a significant force exerted on the piezo-electric stack by a striker 8 driven by the power spring 10. The short duration of the strike generates an impulse with wide frequency content which aids in coupling of the mechanical energy into electricity within the piezo-electric material.

OPERATION

Prior to operation, the defibrillator is armed by either pulling shaft 7 by the handle 32 directly or working the lever 9 and ratcheting shaft 7 and striker 8 attached to it into the armed position while compressing power spring 10. In the armed position spring 10 is held in compression by trigger 11 which arrests the movement of striker 8.

Figure 5A:
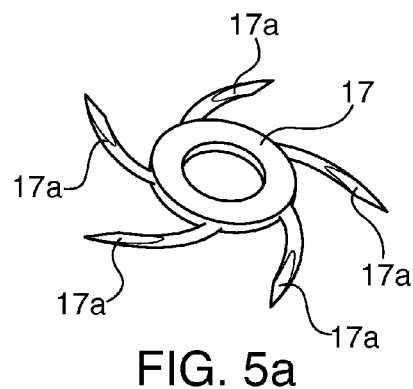
FIG. 5a is a perspective view of an alternate 'return' electrode assembly with scimitar-shaped electrode elements.
Figure 5B:
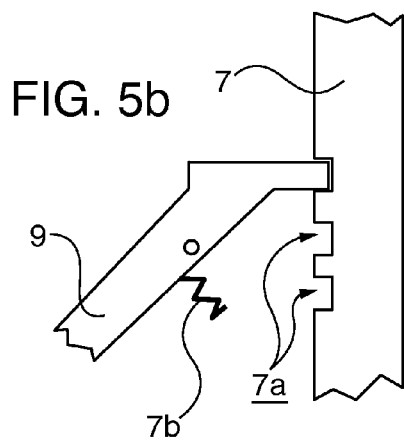
FIG. 5b is a partial cross section of the arming lever interfacing with striker shaft.

To effect ratcheting of shaft 7 lever 9 engages the corresponding notches 7a on shaft 7 as shown on FIG. 5b. Spring 7b returns lever 9 to its starting position to repeat the ratchet operation.

Referring to FIG. 3, after arming, the defibrillator's cardiac electrode 5 is pushed into the patient's body preferably via the $5^{th}$ intercostal space 15, between the $5^{th}$ rib denoted 14, and the $6^{th}$ rib denoted 14a, respectively and engages patient's heart 16 with its exposed conductive tip.

The length of electrode 5 is made such that when it is fully inserted, electrode 13 contacts the skin and pierces it with its sharp spikes 13a thus reducing the electrical impedance for the defibrillation circuit.

Defibrillation function is then initiated by applying pressure to the trigger 11 which releases striker 8. Striker 8 is then propelled by the expanding spring 10 and strikes piezo-electric generator 6 producing an electric pulse which propagates down to patient's heart 16 via electrodes 5 and 11.

After defibrillation pulse the defibrillator is either withdrawn from the patient's body, or a subsequent pulse(s) can be delivered in case the first pulse did not succeed.

ADDITIONAL EMBODIMENTS

In the foregoing description like components are labeled with like numerals.

Referring to FIG. 4 an alternative defibrillator system embodiment 2a utilizes a return electrode 17 instead of 13. Electrode 17 is shown in detail on FIG. 5a where in addition to the central annular portion it contains a number of scimitar-shaped sharp electrode elements 17a extending radially from the common center. These elements are inclined with respect to the plane of the device to facilitate their piercing of patient's skin when the defibrillator body 4 and the attached electrode 17 are placed upon the patient's skin and rotated, in this embodiment, clockwise. Rotating defibrillator body 4 counter-clockwise removes electrode elements 17a from the skin.

Figure 6:
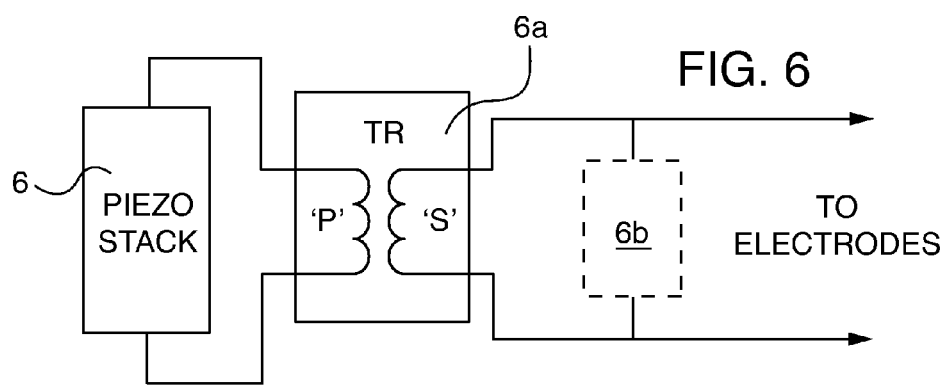
FIG. 6 is an electrical schematic of the system's output impedance matching and pulse shaping network.
Figure 6A:
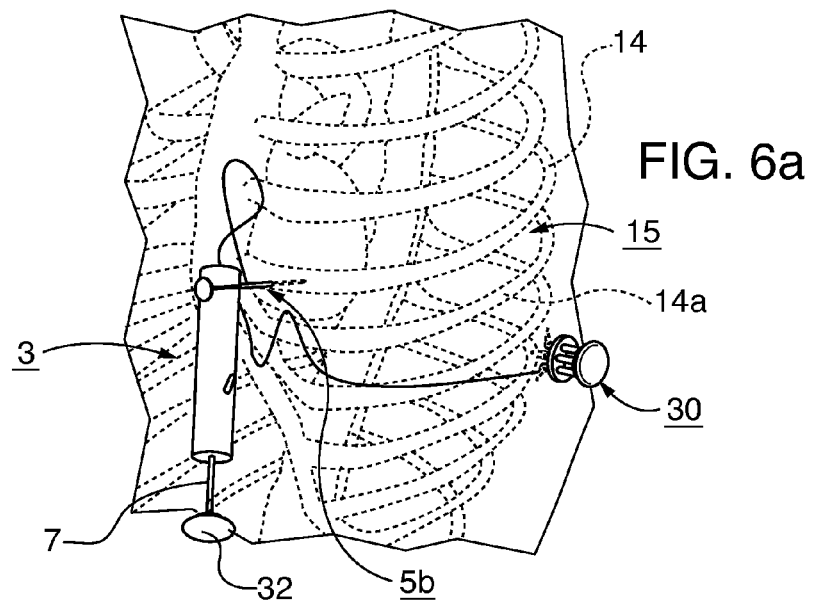
FIG. 6a is a perspective view of the defibrillation system's alternate embodiment with direct cardiac and indirect subcutaneous electrodes assemblies positioned on the patient's thorax.
Figure 6B:
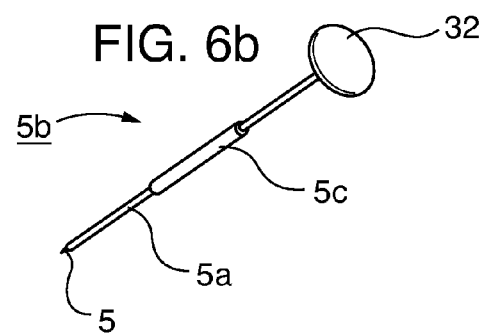
FIG. 6b is a perspective view of the direct cardiac electrode assembly.

Referring to FIG. 6a an alternative defibrillator system embodiment 3 utilizes detachable direct cardiac electrode assembly 5b and indirect subcutaneous electrode assembly 30. Direct cardiac electrode assembly 5b shown on FIG. 6b is similar in construction to electrode 5 with the addition of the handle 32 and guidance sleeve 5c which facilitates precise aiming of the electrode to the heart.

Figure 7A:
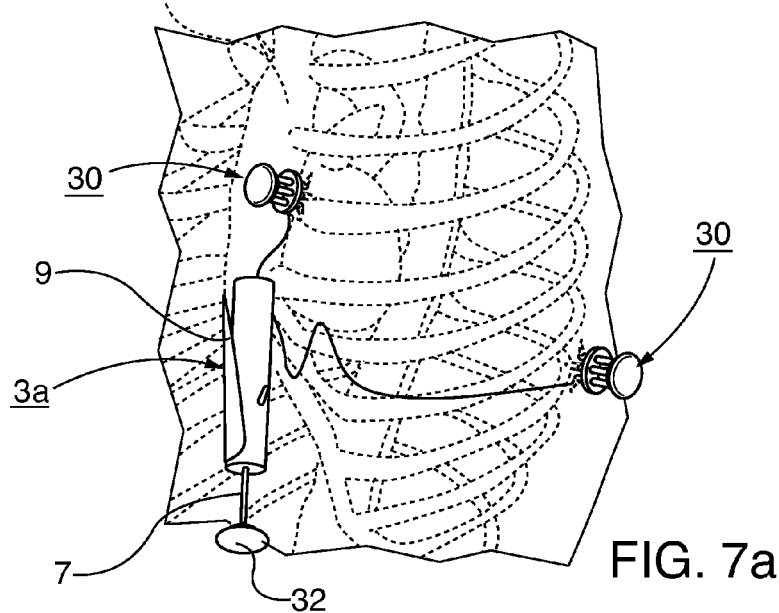
FIG. 7a is a perspective view of the defibrillation system's alternate embodiment with indirect subcutaneous electrode assemblies positioned on the patient's thorax.
Figure 7:
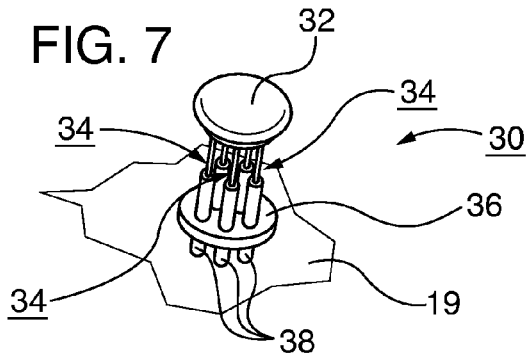
FIG. 7 is a perspective view of the subcutaneous electrode assembly in its pre-deployment configuration.
Figure 8:
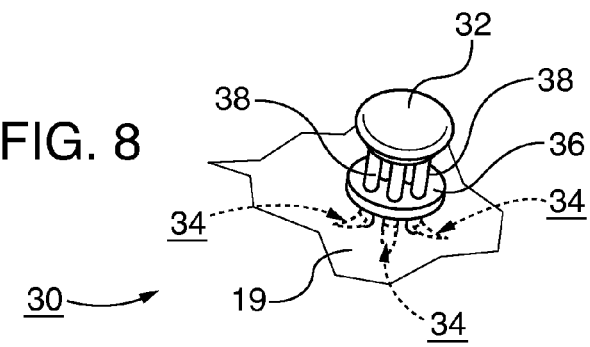
FIG. 8 is a perspective view of the subcutaneous electrode assembly deployed.

An alternative defibrillator system embodiment 3a utilizing indirect subcutaneous electrode assemblies 30 is shown on FIG. 7a. Subcutaneous electrode assemblies 30 are placed onto patient's body, one next to the sternum 18 and the other below left armpit, with their blade electrodes piercing the skin to establish a low-impedance current path to the heart.

Referring to FIGS. 7, 8, 15, 15a, 16 and 16a subcutaneous electrode assembly 30 comprises several electrode sleeves 38 which contain electrode assemblies 34 located in a curved inner channel 35 terminating in electrode exit aperture 35a. Each assembly 34 contains one or more flexible blade electrodes 34a connected to the contact pad 34b which in turn is electrically connected to defibrillator 3. Contact pad 34b is also mechanically connected to the deployment handle 32. Flexible electrode's 34a tip is made to be very sharp to facilitate its easy penetration into the skin. Several sleeve-electrode assemblies are held together by plate 36.

Upon placement on the patient's skin 19, handle 32 is pressed downwards toward the skin's surface by the operator. Sleeves 38 internal curved channels 35 terminating in outwardly and radially pointing apertures 35a force blade electrodes 34a to emerge at a slant angle with respect to the skin surface 19, penetrating it. One or more electrodes 34a are thus inserted simultaneously under the skin enabling a low-impedance current path for successful defibrillation.

Figure 9:
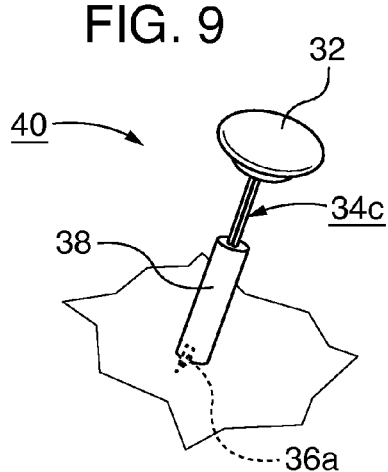
FIG. 9 is a perspective view of the subcutaneous electrode assembly's alternate embodiment in its pre-deployment configuration.
Figure 10:
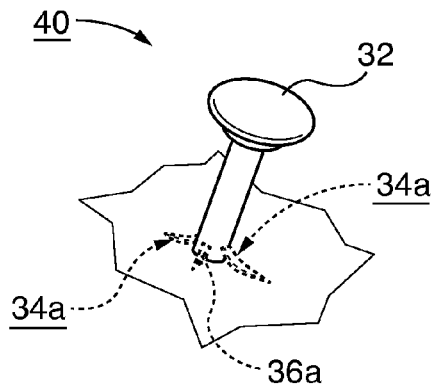
FIG. 10 is a perspective view of the subcutaneous electrode assembly's alternate embodiment while deployed.
Figure 11:
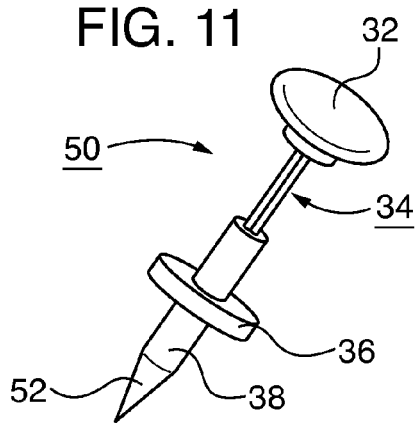
FIG. 11 is a perspective view of a subcutaneous electrode assembly's alternate embodiment in its pre-deployment configuration.
Figure 12:
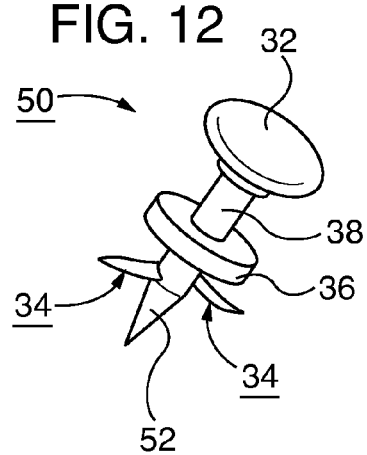
FIG. 12 is a perspective view of a subcutaneous electrode assembly's alternate embodiment while deployed.
Figure 13:
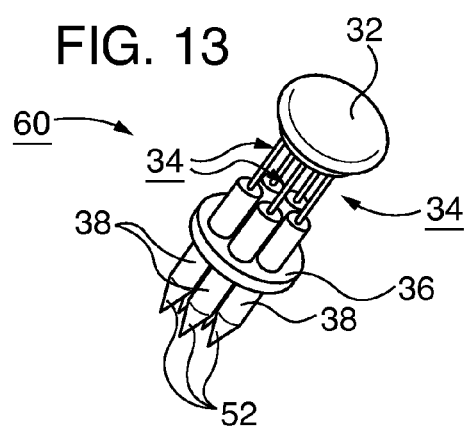
FIG. 13 is a perspective view of another subcutaneous electrode assembly's alternate embodiment in its pre-deployment configuration.
Figure 14:
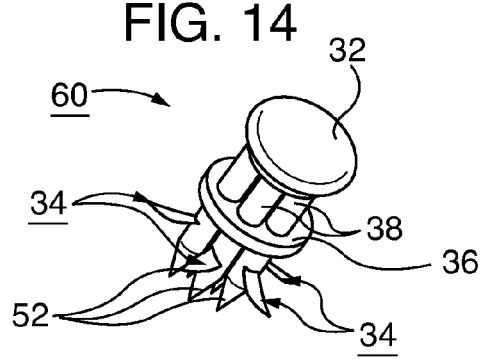
FIG. 14 is a perspective view of another subcutaneous electrode assembly's alternate embodiment while deployed.
Figure 15:
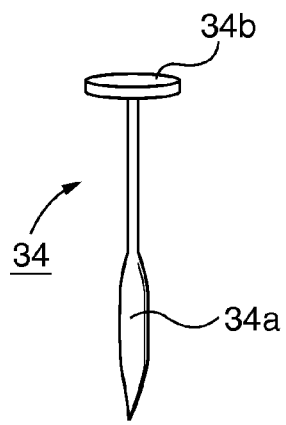
FIG. 15 is a perspective view of a subcutaneous electrode element in pre-deployment configuration.
Figure 15A:
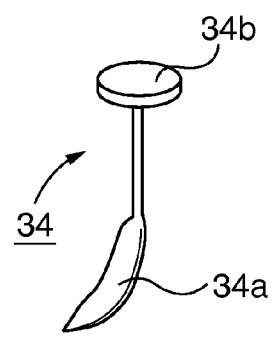
FIG. 15a is a perspective view of a subcutaneous electrode element while deployed.
Figure 16:
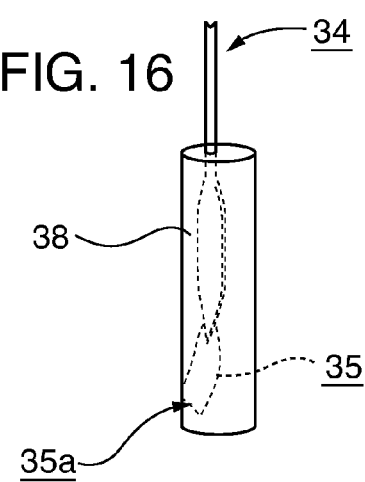
FIG. 16 is a perspective partial view of a subcutaneous electrode assembly in pre-deployment configuration.
Figure 16A:
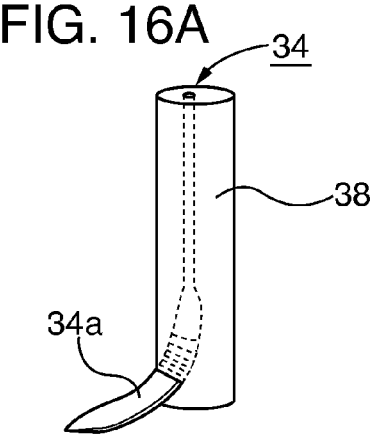
FIG. 16a is a perspective partial view of a subcutaneous electrode assembly while deployed.

FIGS. 9 and 10 show an alternate embodiment of the subcutaneous electrode assembly 40. It is more compact than assembly 30 and utilizes a single sleeve 38 with assembly 34c consisting of two electrodes 34. To stabilize the assembly on the patient's skin, it is equipped with a rest 36a on its bottom.

Yet another embodiment of the subcutaneous electrode assembly 50 is shown on FIGS. 11 through 14. Instead of the flat bottom of the previous assembly, each sleeve 38 terminates in a sharp tip 52. This construction enables initial penetration of the skin and subcutaneous layers prior to deployment of sharp electrodes 34a. The plate 36 in addition of holding sleeves 38 serves in this embodiment as their penetration depth limiter.

Figure 17:
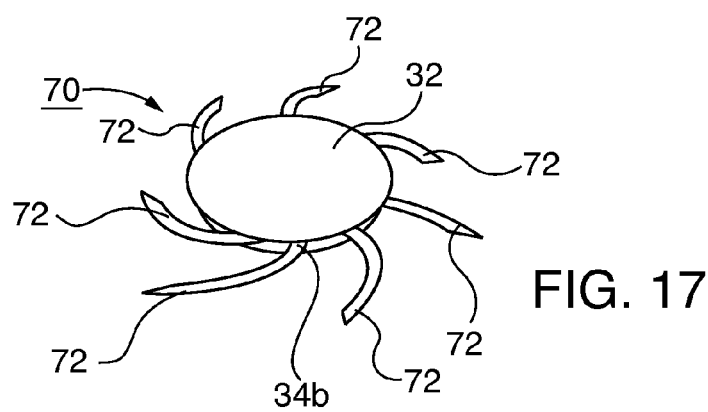
FIG. 17 is a perspective view of a subcutaneous electrode with scimitar-shaped electrode elements.
Figure 21:
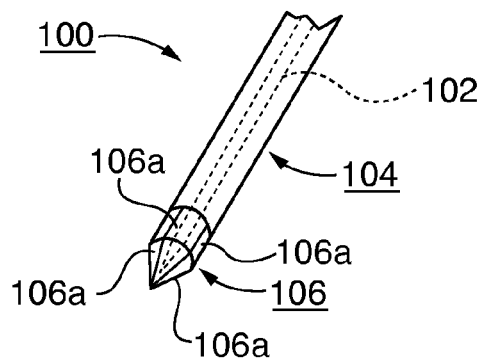
FIG. 21 is a partial perspective view of a linear subcutaneous electrode assembly inside the introducer, with introducer penetrating tip closed.
Figure 22:
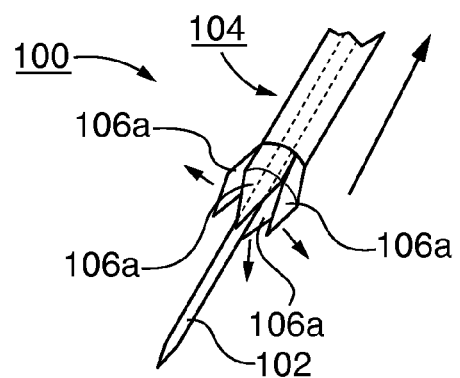
FIG. 22 is a partial perspective view of a linear subcutaneous electrode assembly inside the introducer, with introducer penetrating tip open during extraction.

Another embodiment of the subcutaneous electrode assembly 70 is shown on FIG. 17. It features scimitar-shaped electrodes 72 extending radially from the common contact pad 34b attached to handle 32. The electrodes are inclined to the plane of the handle/contact pad, so when placed on skin 19, they pierce it when handle 32 is turned, in this configuration, clockwise. Rotating handle 32 counter-clockwise removes electrodes 72 from the skin.

Figure 23:
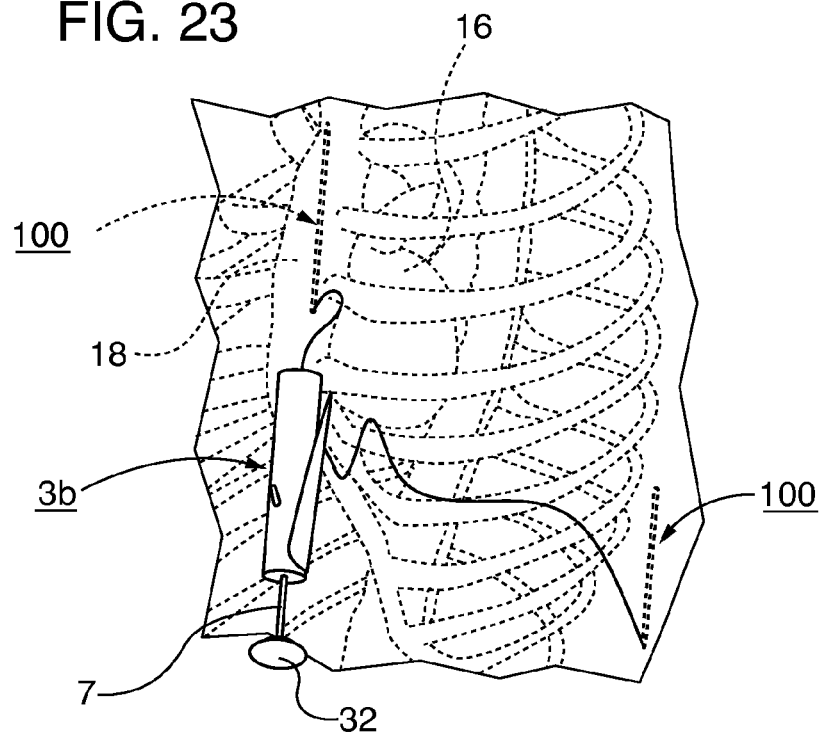
FIG. 23 is a perspective view of the alternate embodiment of the defibrillation system with indirect linear subcutaneous electrode assemblies positioned in the patient's thorax.

Another embodiment of the subcutaneous electrode assembly 100 is shown on FIGS. 19 through 23. A relatively thin and flexible electrode 102 is positioned inside introducer 104 for subcutaneous insertion. Introducer 104 at its distal end has a sharp penetrating tip 106 which consists of several flexible tangs 106a. During insertion tangs 106a are held firmly against each other by skin's resistance, forming a sharp tip 106. Referring to FIG. 23 electrode assemblies 100 of defibrillator system's embodiment 3b are placed under patient's skin preferably at two locations: one along the patient's sternum 18 and another laterally below left armpit. These locations are customarily selected for external defibrillator electrode pads placement and also shown in the prior art implantable defibrillator system 80 with indirect electrode 82 and implantable defibrillator 86 whose metal case serves as a second electrode, shown on FIG. 18. Afterwards, introducers 104 are withdrawn and electrodes 102 are left in place. Specifically, when an electrode assembly 100 is positioned at the desired location, introducer 104 is withdrawn by the operator's pulling it back off of the electrode 102. During this operation the tip of electrode 102 pushes tangs 106a of introducer 104 outwards and causes them to flex, clearing electrode 102. Introducer 104 is then slid off the electrode 102, leaving it in place inside patient's body. Electrode 102 is then electrically connected to the defibrillator's piezo-electric generator 6. Upon completion of defibrillation electrodes 102 are withdrawn from the patient's body by simple pulling.

Although descriptions provided above contain many specific details, they should not be construed as limiting the scope of the present invention. Several features of distinct embodiments can be combined, for example, the introducer 104 type can be used with direct cardiac contact electrode 5, with an advantage that a thin electrode can be substituted instead of a more robust one. A thin electrode then can be left in place while chest compressions are performed as part of a cardio-pulmonary resuscitation (CPR) procedures.

Various piezo-electric materials can be utilized in the piezo-electric generator 6, as well as different number and geometry of the individual piezo-electric stack elements. Also, the manner of inducing stress in the generator piezo-electric stack can range between longitudinal compression as in instant invention, via bending by a transverse force, or combination thereof. Also, the behavior of piezo-electric materials depends on the relative direction of the applied stress and material's crystallographic axes.

Additionally, the design of striker 8 itself and case 4 it travels in can be optimized to improve striker's acceleration by decreasing friction and air resistance. Thus, the inside of case 4 can be polished and striker 8 sides coated with a low-friction material, either temporary like oil or grease, or permanent, such as a fluoropolymer coating like Teflon®. To minimize air compression and resistance longitudinal through holes can be created in the striker to permit air escape. Through holes can be provided in the case 4 wall at its top and bottom to permit air escape in front of the moving striker 8, and air ingestion behind it.

In addition, the compressed spring-type energy storage can be substituted by a compressed air or $CO_2$ in a compact cylinder.

The specific implementations disclosed above are by way of example and for enabling persons skilled in the art to implement the invention only. I have made every effort to describe all the embodiments we have foreseen. There may be embodiments that are unforeseeable or which are insubstantially different. I have further made every effort to describe the invention, including the best mode of practicing it. Any omission of any variation of the invention disclosed is not intended to dedicate such variation to the public, and all unforeseen or insubstantial variations are intended to be covered by the claims appended hereto. Accordingly, the invention is not to be limited except by the appended claims and legal equivalents.

I claim:

1. A method of external cardiac defibrillation wherein at least two electrodes, namely a first electrode and a second electrode, are connected to a piezo-electric source, said piezo-electric source located outside patient's body, wherein said first and said second electrode each are introduced into said patient's body deeper than said patient's outer skin layer, wherein said electrodes are capable of forming a closed electrical circuit from said piezo-electric source to said first electrode, through said patient's body to said second electrode, back to said piezo-electric source, wherein said piezo-electric source comprises a piezo-electric generator, wherein electrical energy is generated by applying mechanical stress to said piezo-electric generator, wherein an electrical current from said piezo-electric generator is passed through said patient's heart to effect defibrillation, wherein electrical impedance of said patient's skin is bypassed by said electrodes.

2. The method of claim 1, whereby at least one of said electrodes is inserted subcutaneously by movement essentially perpendicular to said patient's skin surface.

3. The method of claim 1, whereby at least one of said electrodes is inserted subcutaneously by movement essentially oblique to said patient's skin surface.

4. The method of claim 1, whereby at least one of said electrodes further comprises at least one introducer element, said element capable of penetrating said patient's skin, said element assisting in placement of said electrode within said patient's body.

5. The method of claim 4, wherein said introducer element movable with respect to said electrode to electrically expose said electrode upon subcutaneous placement of said electrode.

6. The method of claim 1, wherein the piezo-electric source further comprises electrical pulse conversion elements.

7. A method of external cardiac defibrillation wherein at least one electrical pulse is applied directly to the patient's heart, wherein at least two electrodes, namely a first electrode and a second electrode, are connected to a piezo-electric source, wherein said piezo-electric source is located externally to patient's body, wherein said first electrode is inserted into said patient's body, wherein said first electrode contacts said patient's heart, wherein said second electrode is inserted subcutaneously into said patient's body, wherein said piezo-electric source comprises a piezo-electric generator, wherein said electrical pulse is generated by applying mechanical stress to said piezo-electric generator, wherein said electrical pulse is transmitted from said electrical source to said first electrode through said patient's heart to said second electrode back to said piezo-electric source.

8. The method of claim 7, whereby said first electrode comprises an elongated conductor element, said conductor electrically insulated along its length except its distal tip.

9. The method of claim 7, wherein the piezo-electric source further comprises electrical pulse conversion circuitry.

10. The method of claim 7 wherein said second electrode is inserted subcutaneously into said patient's body by movement essentially perpendicular to said patient's skin surface.

11. The method of claim 7 wherein said second electrode is inserted subcutaneously into said patient's body by movement essentially oblique to said patient's skin surface.

12. An external cardiac defibrillation system comprising a piezo-electric source located outside patient's body, said piezo-electric source further comprising a piezo-electric generator and at least two electrodes connected thereto, whereby at least one of said electrodes comprises a penetrating element, wherein said penetrating element is inserted into said patient's body, wherein said penetrating element contacts said patient's heart, wherein said second electrode is inserted subcutaneously into said patient's body, wherein said piezo-electric source comprises a piezo-electric generator, wherein an electrical pulse is generated by applying mechanical stress to said piezo-electric generator, wherein said electrical pulse is transmitted from said electrical source to said first electrode through said patient's heart to said second electrode back to said electrical source, and wherein said piezo-electric source and said electrodes comprise an integrated assembly.

13. The electrodes of claim 12, whereby at least one of said electrodes further comprises introducer element, said introducer assisting penetration of the patient's skin and subcutaneous positioning of said electrode.

14. The introducer element of claim 13, said introducer element movable with respect to said electrode to electrically expose said electrode upon subcutaneous placement of said electrode.

15. The penetrating element of claim 12, whereby said element is capable of penetrating patient's body and electrically contacting said patient's heart.

16. The penetrating element of claim 15 further comprising an electrical conductor of essentially elongated shape, said conductor electrically insulated along its length except for its distal tip.

17. The piezo-electric source of claim 12 further comprising electrical pulse conversion circuitry.

\* \* \* \* \*